United States Patent [19]
Ash

[11] Patent Number: 5,944,520
[45] Date of Patent: Aug. 31, 1999

[54] DENTAL HAND PIECE WITH INTERNAL BACK FLOW PREVENTION VALVE

[76] Inventor: Albert Ash, 2437 E. 53rd St., Los Angeles, Calif. 90058

[21] Appl. No.: 08/922,139

[22] Filed: Aug. 29, 1997

Related U.S. Application Data

[63] Continuation-in-part of application No. 08/705,564, Aug. 29, 1996, abandoned.

[51] Int. Cl.$^6$ .......................................... A61C 1/10
[52] U.S. Cl. ............................................. 433/84; 433/126
[58] Field of Search ................................ 433/84 OR, 85, 433/114, 126

[56] References Cited

U.S. PATENT DOCUMENTS

| | | | |
|---|---|---|---|
| 4,026,025 | 5/1977 | Hunt | 433/80 |
| 4,117,597 | 10/1978 | Trist et al. | 433/126 |
| 4,957,483 | 9/1990 | Gonser et al. | 433/80 |
| 5,088,924 | 2/1992 | Woodward | 433/29 |
| 5,342,195 | 8/1994 | Davis et al. | 433/80 |
| 5,407,352 | 4/1995 | Kawata | 433/84 |
| 5,464,350 | 11/1995 | Bierbaum | 433/84 |
| 5,501,596 | 3/1996 | Bailey | 433/86 |

FOREIGN PATENT DOCUMENTS

| | | | |
|---|---|---|---|
| 0271597 | 6/1988 | European Pat. Off. | 433/114 |
| 4141161 | 5/1992 | Japan | 433/114 |
| 6098989 | 4/1994 | Japan | 433/132 |

*Primary Examiner*—John J. Wilson
*Attorney, Agent, or Firm*—James E. Brunton

[57] ABSTRACT

A fully autoclavable dental-hand-piece assembly which includes a unique, highly miniaturized, internally disposed, one-way check valve that effectively prevents microbial contamination from reaching the cooling fluid supply lines that provide cooling fluid to the unit. The one-way check valve is specially designed to be able to effectively withstand the high temperatures required in the autoclaving step to which the hand piece, including the check valve, is exposed. Uniquely, the one-way check valve can readily be installed either within the hollow handle of a conventional dental hand piece or within a conventional, universal dental-hand-piece coupler without the necessity of making any substantial modification to the design of the hollow handle or the universal coupler. Also disclosed is a novel coupler assembly for coupling together the hand piece and the air and water supply lines. In one form of the invention, the coupler embodies easily removable air and water valves which function to prevent back flow of contaminants into the supply lines.

20 Claims, 11 Drawing Sheets

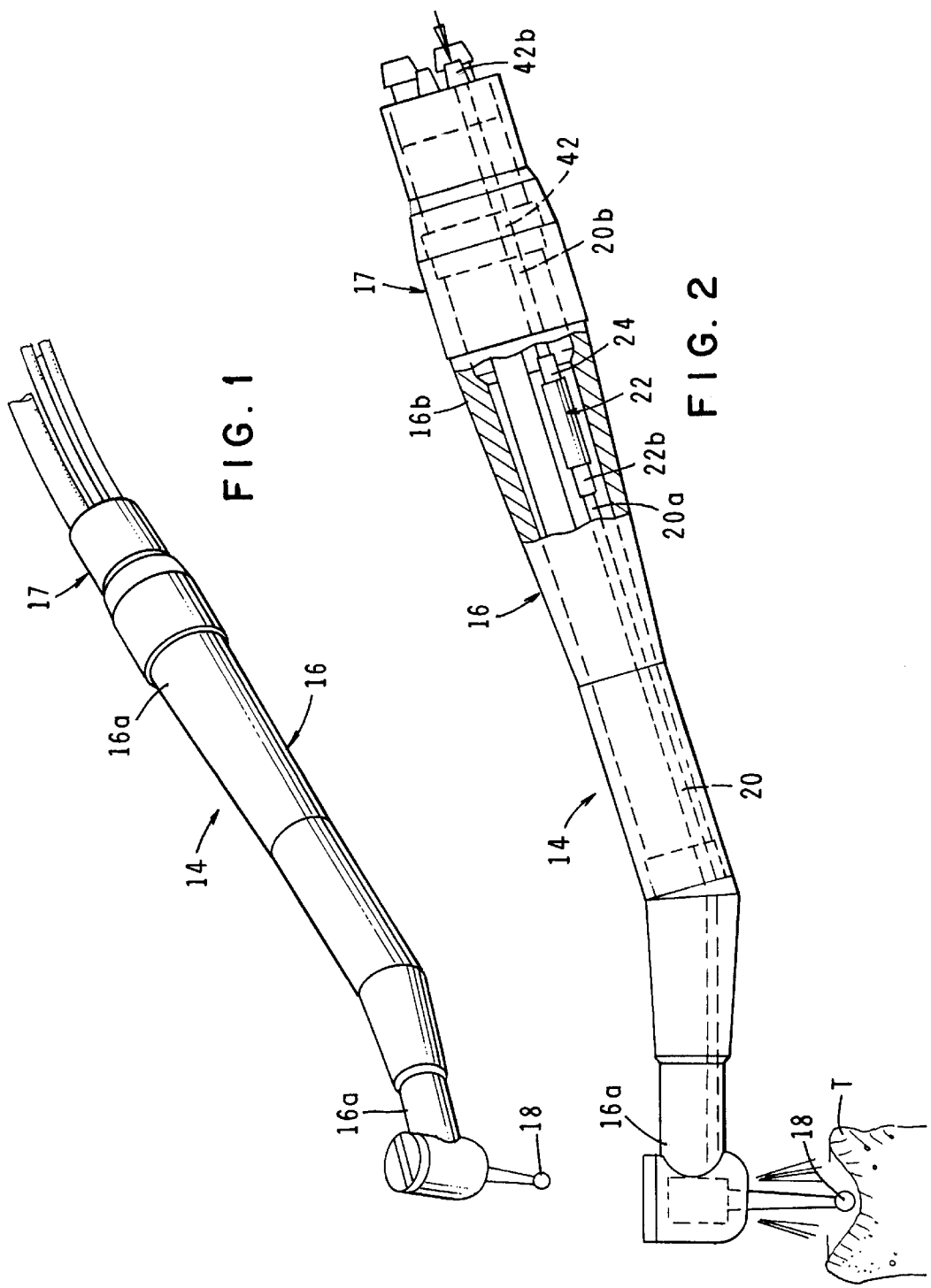

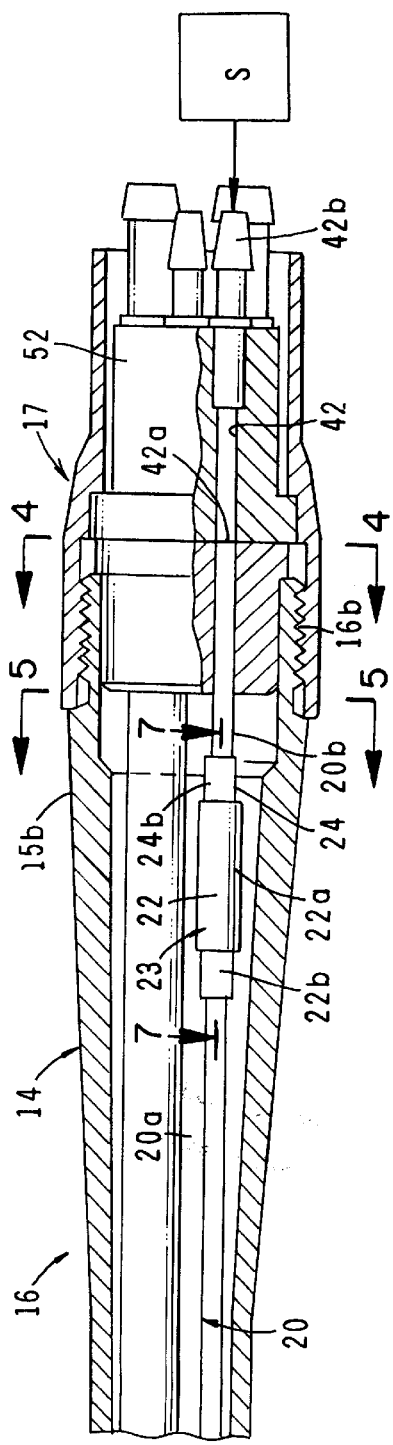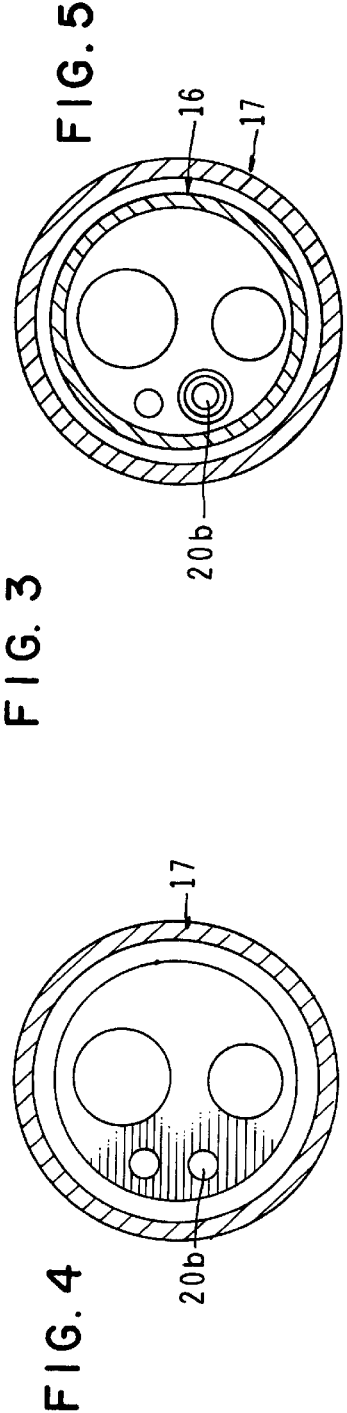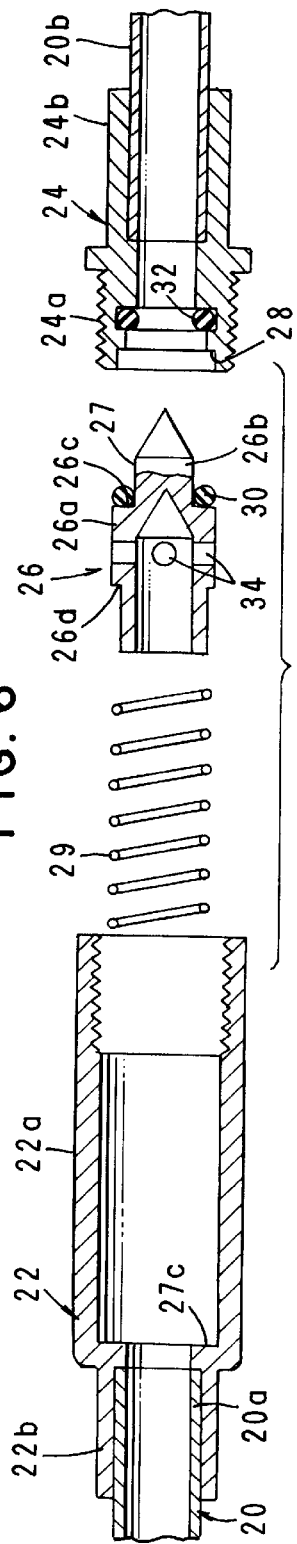

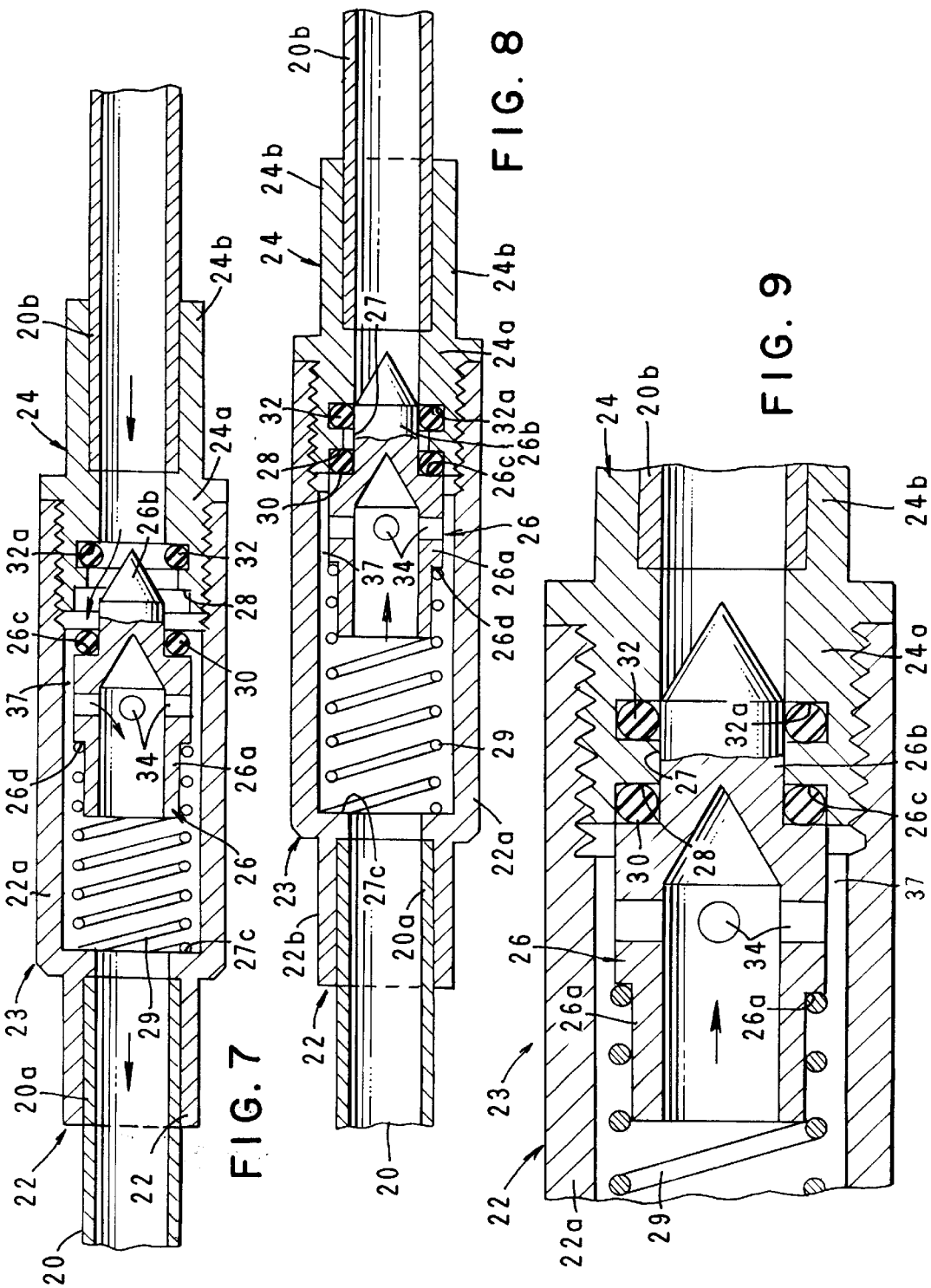

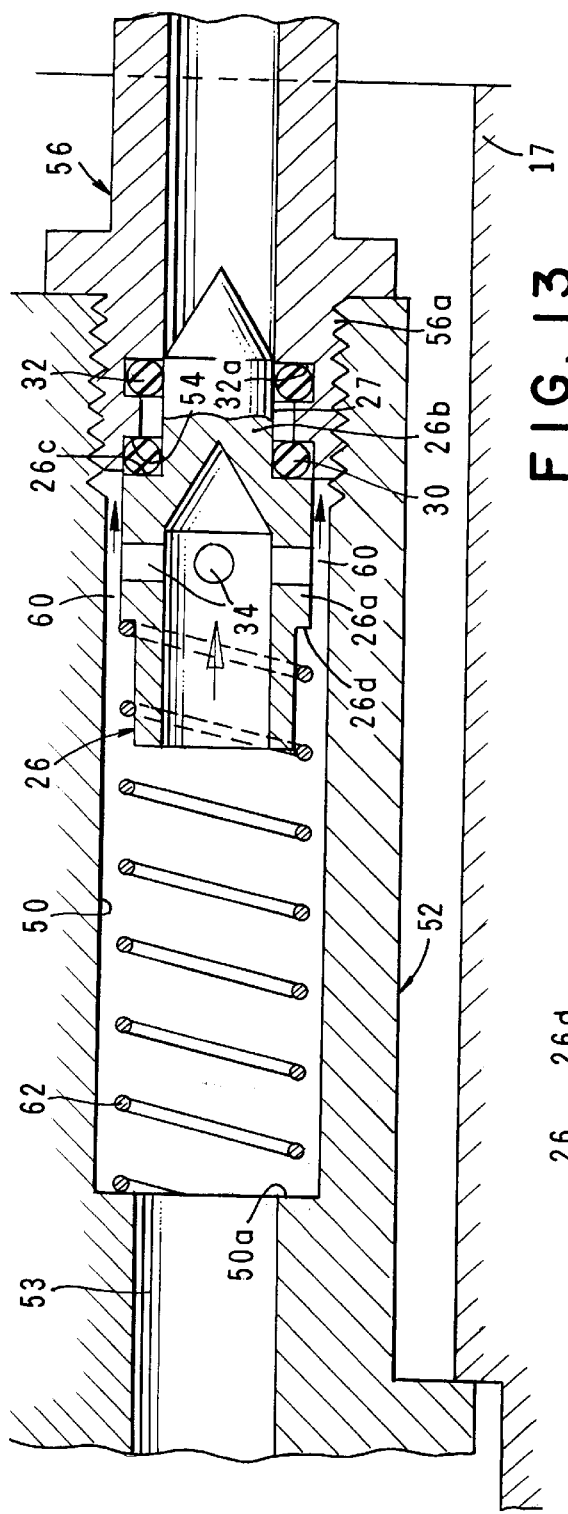
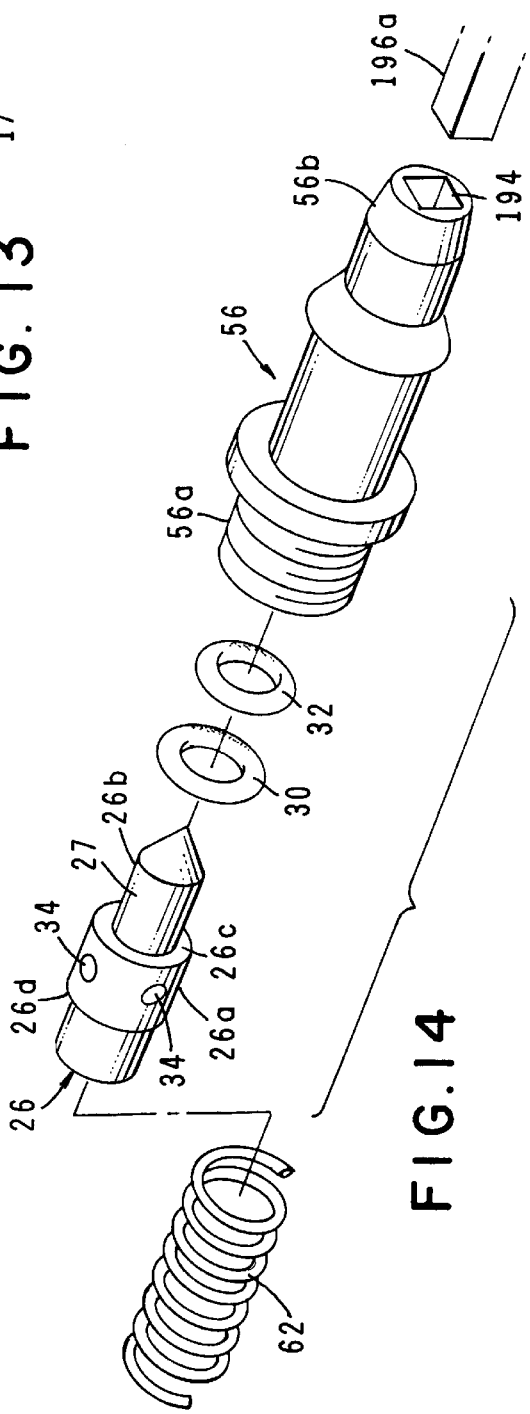
FIG. 13
FIG. 14

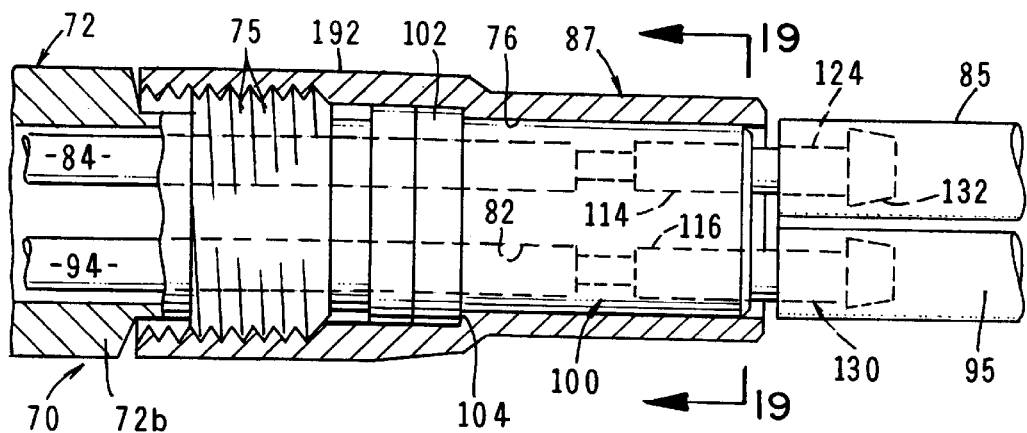
FIG. 18
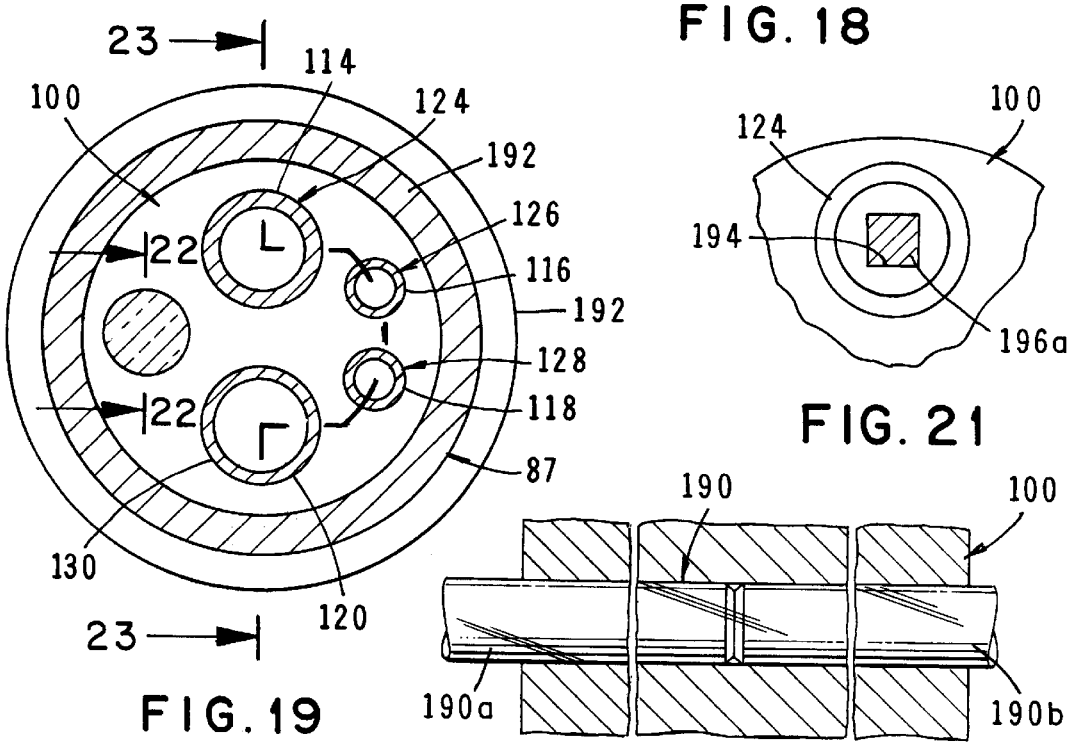
FIG. 19
FIG. 21
FIG. 22
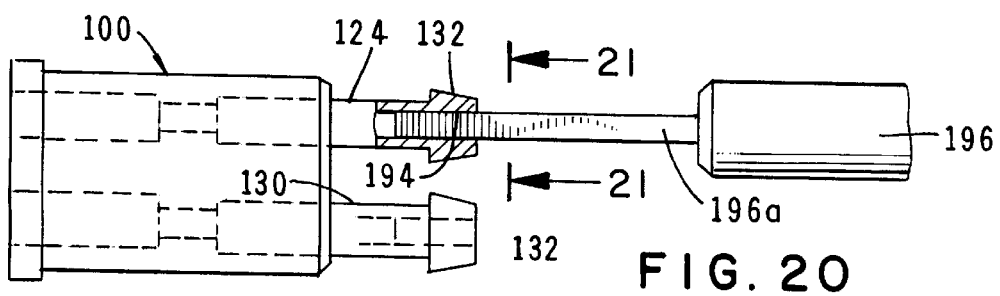
FIG. 20

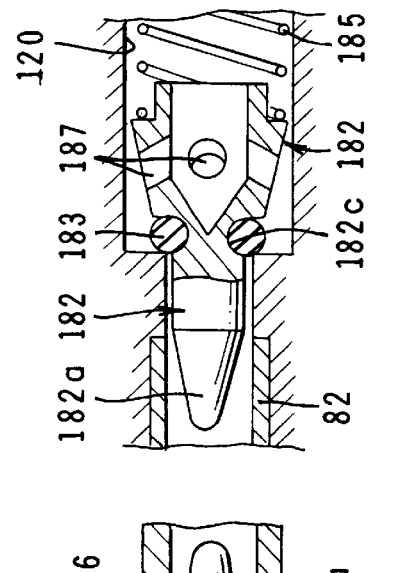
FIG. 27
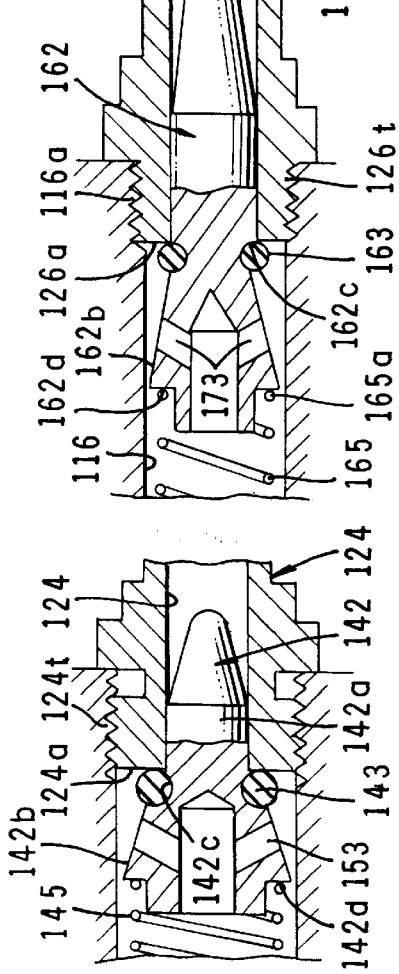
FIG. 26
FIG. 25
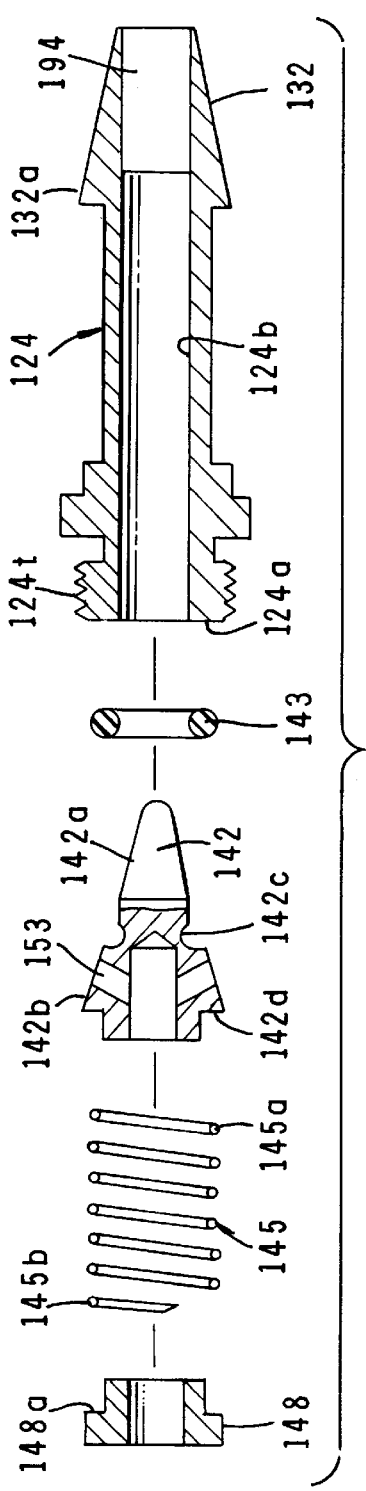
FIG. 28

DENTAL HAND PIECE WITH INTERNAL BACK FLOW PREVENTION VALVE

This is a Continuation-In-Part of U.S. application, Ser. No. 08/705,564, filed Aug. 29,1996, now abandoned.

BACKGROUND OF THE INVENTION

1. Field of the Invention

The present invention relates generally to dental hand pieces. More particularly, the invention concerns a dental hand piece and the method of making the same having a novel safety check valve embodied in the housing thereof that positively prevents back flow of bacterial contaminants through the hand piece.

2. Discussion of the Invention

Microbial contamination of dental unit water lines has recently been recognized as being a potentially serious health problem. More particularly, recognition of the substantial biohazards involved in disposing and aerosolizing suspensions of water borne microorganisms, some of them pathogenic, has created considerable concern on the part of the dental profession as well as various federal agencies, including The Centers for Disease Control and Prevention.

Contamination of the dental unit water lines is due in large measure to "suck back" from the open tips of conventional air-water type hand pieces. In this regard, tests have shown that up to 900 micro liters of contaminated oral fluids and other detritus generated during a dental procedure can be drawn up to several feet into the water line of the unit. Additionally, the problem may be further complicated by the occurrence of complex hydra-dynamic phenomena at the exposed tip of the waterline especially when pressurized flow is abruptly stopped leading to the possibility of passive retraction of the contaminated oral fluids.

Several infection control procedures have been suggested in the past which are directed toward mitigating the serious problem of microbial contamination of dental unit waterlines. One of these control procedures suggests the step of a positive discharge of water from the hand piece for several minutes after each dental procedure and at the beginning of the clinic day. However, this procedure has proven to be generally unsatisfactory and, in fact, may lead to an increase in microbial contaminant levels due to the dislodging of flakes of biofilm from the tubing wall during the flushing operation.

Another control approach, which has been suggested by some agencies, involves the use of sterile water during the performance of surgical procedures within the oral cavity. This approach has generally not been adopted by the practicing dentists due to the unavailability of sterile water at the dental surgery situs. Still another suggested infection control procedure involves the use of biocidal rinses or flushes both during and after the dental procedure. However, the use of such biocidal agents typically requires prior approval by the Food and Drug Administration which approval has not readily been obtainable.

In summary, the infection control procedures that have been proposed in the past have been generally ineffective and, until now, the serious problems of microbial contamination of dental unit water lines remains basically unsolved. It is against this background that the present inventor sought to, and did in fact, solve the difficult problem of control of microbial contamination of dental unit water lines.

SUMMARY OF THE INVENTION

By way of summary, one embodiment of the present invention comprises a highly novel dental-hand-piece assembly which includes a unique, miniaturized, one-way check valve disposed internally of the hand piece. The hand piece assembly of the invention, including the miniaturized check valve, is specially designed to withstand elevated temperatures within a range sufficient to sterilize the entire assembly. One form of apparatus of the present invention, comprises a conventional type of dental hand piece having a first end to which a cutting element can be operably interconnected, and a second end to which a source of cooling fluid can be interconnected. Extending throughout the length of the unit is a fluid conduit which communicates at one end with the source of cooling fluid and at the other end dispenses cooling water in a direction toward the cutting element. The novel, one-way check valve of the apparatus is specifically designed to be interposed within the fluid conduit of a conventional dental hand piece and, when in place, functions, when the valve is open, to permit fluid flow in a first direction toward the cutting element, but, when the valve is closed, effectively blocks fluid flow in a second opposite direction toward the source of cooling water.

With this novel construction, any contaminated cooling fluid which may be suctioned back into the outlet of the fluid conduit is blocked by the one-way check valve and effectively prevented from flowing into the supply lines which supply the cooling fluid to the unit. Since the dental-handpiece assembly is sterilized by autoclaving after each use, microbial contaminants trapped within the hand piece body or within the check valve are destroyed. Because the elastomeric sealing elements of the check valve are constructed from materials that are not damaged by high temperature, the autoclaving step does not adversely affect the normal continued operation of the one-way check valve.

In one embodiment of the invention, the novel, highly miniaturized check-valve assembly is designed to be interposed within the fluid conduit at a location internally of the hollow handle of the dental hand piece. In an alternate form of the invention, the check-valve assembly is designed to be disposed within a conventional dental-hand-piece coupler of the character that functions to interconnect the source of cooling fluid with the hollow handle of the unit. In either case, the novel check valve of the invention effectively prevents contaminates from reaching the cooling fluid supply lines of the apparatus which, of course, cannot be decontaminated by autoclaving.

With the foregoing in mind, it is an object of the present invention to provide a novel autoclavable dental-hand-piece assembly and the method of making the assembly which includes a unique, highly miniaturized, internally disposed, one-way check valve that effectively prevents microbial contamination from reaching the cooling fluid supply lines that provide cooling fluid to the unit.

Another object of the invention is to provide a dental hand piece of the aforementioned character in which the one-way check valve is specially designed to be able to effectively withstand the high temperatures required in the autoclaving step to which the hand piece, including the check valve, is exposed.

Another object of the invention is to provide a novel, high-temperature resistant, one-way check valve that can readily be installed either within the hollow handle of a conventional dental hand piece or within a conventional, universal dental-hand-piece coupler without the necessity of making any substantial modification to the design of the hollow handle or the universal coupler.

Another object of the invention is to provide a novel dental-hand-piece assembly of the type described in the preceding paragraphs in which the check-valve assembly can be installed during the initial fabrication of the hand piece, or alternatively, can easily be added to existing dental hand piece units as a retrofit component.

Another object of the invention is to provide a method for retrofitting conventional, commercially available dental hand pieces and universal dental hand piece couplers to install therewithin the novel miniaturized one-way check valve of the invention.

Another object of the invention is to provide an autoclavable dental-hand-piece assembly of the character described, which is operated in substantially the same manner as conventional prior art hand piece assemblies, is highly reliable in operation and is inexpensive to manufacture and easy to maintain.

Another object of the invention is to provide a novel, antiretraction, universal hand piece coupler assembly for coupling together any standard type of commercially available, autoclavable hand piece with air and water supply lines. The universal coupler assembly is fully autoclavable and embodies a unique, four-way, replaceable valve system which positively prevents air and water from being drawn back from the hand piece into the supply lines. Additionally, the valve system precludes contaminated exhaust air from being blown into a sterilized hand piece at time of startup.

More particularly, it is an object of the invention to provide within the universal coupler assembly an easily removable, first check valve which allows turbine drive air to flow toward the hand piece drive turbine, but positively prevents the back flow of contaminated air from the hand piece into the air line tubing due to suck back.

Another object of the invention is to provide within the universal coupler assembly a novel, easily removable, second check valve which permits water flow to the hand piece, but stops the back flow of contaminated water from the hand piece into the water supply line.

Another object of the invention is to provide within the coupler assembly a novel, easily removable third check valve which allows chip air to flow toward the hand piece, but prevents all back flow of contaminated chip air into the chip air supply tubing.

Still another object of the invention is to provide a novel coupler assembly of the aforementioned character which further includes a novel fourth check valve which prevents contaminated exhaust air from contaminating a freshly sterilized hand piece at time of startup.

Another object of the invention is to provide a coupler assembly as described in the preceding paragraphs which is compact, easy to use in interconnecting the hand piece with the air and water supply lines, is highly reliable in operation and is specially designed to enable quick and easy replacement of the individual check valve assemblies that are removably housed within the coupler body.

BRIEF DESCRIPTION OF THE DRAWINGS

FIG. 1 is a generally perspective view of one form of the dental-hand-piece assembly of the present invention.

FIG. 2 is an enlarged, side-elevational view of the dental-hand-piece assembly partly broken away to show internal construction and to show the interconnection of the back flow prevention valve of the present invention within the fluid flow conduit of the device.

FIG. 3 is a greatly enlarged, side-elevational, cross-sectional view of the right-hand portion of the dental-hand-piece assembly shown in FIG. 2.

FIG. 4 is a cross-sectional view taken along lines 4—4 of FIG. 3.

FIG. 5 is a cross-sectional view taken along lines 5—5 of FIG. 3.

FIG. 6 is a greatly enlarged, side-elevational, cross-sectional, exploded view of one form of the back flow prevention or one-way check valve assembly of the apparatus of the invention.

FIG. 7 is a cross-sectional view taken along lines 7—7 of FIG. 3.

FIG. 8 is a cross-sectional view similar to FIG. 7 but showing the valve member of the back flow prevention valve in a closed position.

FIG. 9 is a greatly enlarged, cross-sectional view similar to FIG. 8 also showing in greater detail the back flow prevention valve in a closed position which prevents reverse flow of cooling fluid toward the inlet port of the dental-hand-piece assembly.

FIG. 13 is a greatly enlarged, side-elevational, cross-sectional view similar to FIG. 12, but showing the back flow prevention valve of the invention in a closed position.

FIG. 14 is a generally fragmentary, exploded view of the back flow prevention or one-way check valve assembly of the present invention.

FIG. 18 is a greatly enlarged, fragmentary, side-elevational view of the right-hand end portion of the dental hand piece illustrating the use of the coupler assembly to operably interconnect the hand piece with the various supply lines.

FIG. 19 is an enlarged, cross-sectional view taken along lines 19—19 of FIG. 18.

FIG. 20 is a fragmentary, side-elevational view of the coupler assembly of the invention partly in cross section to illustrate the interconnection of a wrench with one of the valve assemblies.

FIG. 21 is a cross-sectional view taken along liens 21—21 of FIG. 20.

FIG. 22 is a cross-sectional view taken along lines 22—22 of FIG. 19.

FIG. 25 is an enlarged, cross-sectional view of the upper or first valve shown in FIG. 23.

FIG. 26 is an enlarged, cross-sectional view showing the construction of the intermediate second and third valves of the invention illustrated in FIG. 23.

FIG. 27 is an enlarged, cross-sectional view of the lower or fourth valve shown in FIG. 23.

FIG. 28 is an enlarged, cross-sectional, exploded view of the first valve shown in FIG. 23.

DISCUSSION OF THE INVENTION

Figure 10:
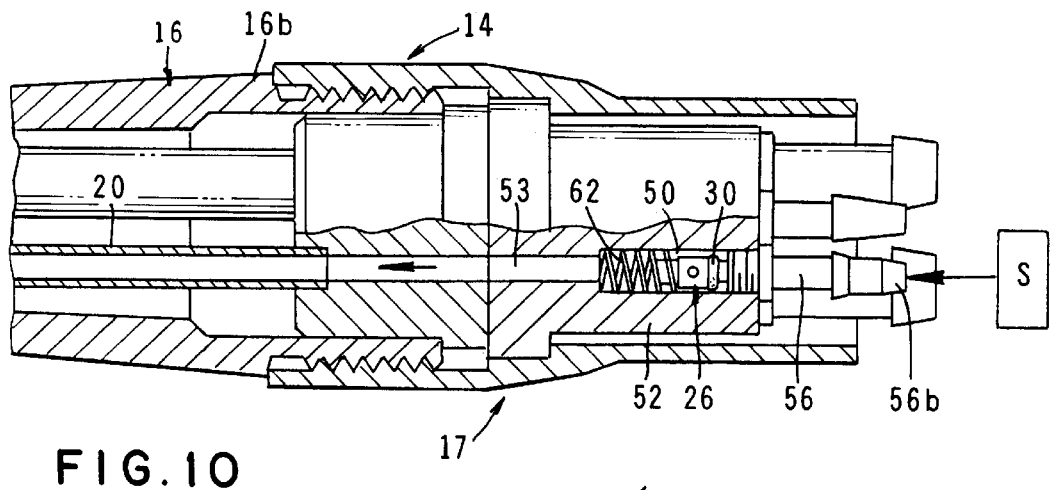
FIG. 10 is a fragmentary, side-elevational, cross-sectional view of an alternate form of the dental-hand-piece assembly of the present invention showing the one-way check valve of the invention installed within the universal hand piece coupler portion of the assembly rather than within the hollow handle portion thereof.
Figure 11:
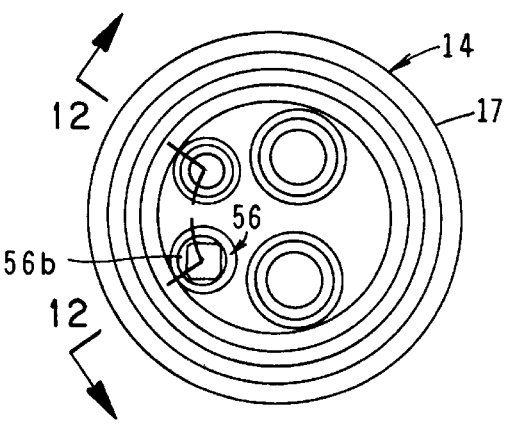
FIG. 11 is a right end view of the apparatus shown in FIG. 10.

Referring to the drawings and particularly to FIGS. 1 through 6, one form of the dental-hand-piece assembly of the present invention is there illustrated and generally designated by the numeral 14. The hand piece itself is of conventional construction and is capable of withstanding elevated temperatures sufficient to sterilize the entire assembly. As best seen in FIGS. 2 and 3, the hand piece comprises a hollow housing 16 having a first end 16a to which a rotatable cutting element 18 can be operably affixed (FIG. 2). A fluid conduit 20 is disposed internally of the hand piece assembly and extends from a location proximate first end 16a thereof to a location proximate end 16b thereof so that it can be operably interconnected with a source of cooling fluid "S" (FIG. 3) via a universal adapter unit 17. Cooling fluid entering conduit 20 will flow along the length of the conduit and will be directed toward the work area or tooth "T" in the manner illustrated in FIG. 2.

Forming an extremely important aspect of the apparatus of the present invention is the valve means of the invention which is interconnected with fluid conduit 20 intermediate the inlet and outlet thereof for permitting flow in a first direction toward first end 16a of the assembly, while blocking fluid flow in a second opposite direction. As is best seen in FIG. 6, the valve means of the invention comprises a first tubular member 22 having an enlarged diameter portion 22a and a reduced diameter first connector sleeve portion 22b which is adapted to be sealably interconnected with an end 20a of conduit 20. Threadably interconnected with first tubular member 22 to form a valve containing body 23 (FIG. 7) is a second tubular member 24 which includes a threaded diameter portion 24a and a non-threaded reduced diameter second connector sleeve portion 24b. Portion 24b is sealably interconnected by any suitable means such as adhesive bonding, soldering or brazing within connector sleeve portion 20b of fluid conduit 20. Also comprising a part of the valve means of the form of the invention shown in the drawings, is a valve member 26 which is reciprocally movable within first tubular portion 22 from a first valve-open position, shown in FIG. 7, which permits fluid flow in a direction toward cutting tool 18, and a second valve-closed position, shown in FIGS. 8 and 9, wherein the valve member is in sealing engagement with a valve seat 28 provided on valve member 24. When valve member 26 is in this second position, fluid flow in a direction toward the source of cooling fluid "S" is blocked. Valve member 26 includes an enlarged diameter portion 26a and a reduced diameter portion 26b, which portions join at a shoulder 26c. circumscribing reduced diameter portion 26b is an elastomeric O-ring 30 which sealably engages seat 28 when the valve member is in the second valve closed position shown in FIG. 8. As illustrated in FIG. 8, when valve member 26 is in the second valve closed position, a second elastomeric O-ring 32, which is held captive in an O-ring groove 32 formed in member 24, sealably engages the external, cylindrical surface 27 of reduced diameter portion 26b of the valve member. With this construction, when the valve is in the closed position, a double seal is provided to prevent leakage of fluid in a direction toward the source of cooling fluid "S". More particularly, as best seen in FIG. 9, elastomeric O-ring 30 is specially designed to seal against seat 28, while elastomeric O-ring 32 is specially designed to seal against the external, cylindrical surface 27 of reduced diameter portion 26b.

Biasing means, shown in the drawings as a coil spring 29, is disposed within member 22 and acts against shoulders 27c and 26d (FIG. 7) to continuously urge valve member 26 toward a valve closed position. Spring 29 is constructed so that cooling water flowing through conduit 20 toward cutting tool 18 will overcome the urging of the spring and thereby maintain the valve in an open condition. However, any back flow of fluid in a direction toward the source "S" will cause the valve to automatically close.

Referring to FIG. 7, it is to be noted that enlarged diameter portion 26a of valve member 26 is provided with a plurality of radially extending fluid passageways 34 which provide fluid flow passageways between the interior of tubular member 22 and the interior of valve member 26. With this construction, when the valve means is in the open position shown in FIG. 7, fluid can flow through end portion 20b of fluid flow conduit 20 into second tubular member 24, past elastomeric O-rings 30 and 32 and into a space 37 located between tubular member 22 and valve member 26. From space 37, the cooling fluid can flow through radial extending flow passageways 34, into the interior of valve member 26, and then into end 20a of fluid flow conduit 20. However, when the valve means is closed, as shown in FIG. 9, flow in a direction toward cooling water source "S" is effectively blocked.

As best seen in FIGS. 1, 2, and 3, the previously mentioned universal dental-hand-piece adapter or coupler 17 is threadably connected to end 16b of hollow handle 16. Adapter 17 is of a generally conventional construction and functions to interconnect fluid conduit 20 with the source of cooling fluid "S". Adapter 17 is of a character that is readily commercially available from a number of sources including the Marmax Company of Bend, Oregon and Berco Products of Los Angeles, Calif. These universal adapter couplings typically include a fluid flow passageway 42 which has an outlet 42a which is adapted to communicate with end 20b of conduit 20 and an inlet end 42b to which a suitable water inlet line (not shown) can be interconnected. In operation, when the universal adapter 17 is interconnected with the handle, or barrel portion of the dental hand piece, a fluid flow path is formed through the dental hand piece assembly so that fluid will flow from the water source "S" through a cooling water line into inlet 42b, through fluid passageway 42 and into fluid conduit 20 of the dental hand piece assembly. Adapter 17 is typically provided with other inlet ports for utilities such as light and air which form no part of the present invention.

In accordance with one form of the method of the invention for retrofitting an autoclavable dental and-piece assembly, the valve means of the invention is interposed within the fluid flow path that extends through the dental-hand-piece assembly in a manner to prevent back flow of fluid in a direction toward the source "S" of the cooling fluid. As will be discussed in greater detail hereinafter, this can be accomplished in two ways, first by interposing the valve means within the fluid conduit 20 that extends through the hollow body portion of the hand piece; or, alternatively, the valve means can be installed within the adapter unit 17.

Considering first the method of the invention whereby the valve means is installed within the fluid conduit 20, the first step in the accomplishment of this method involves cutting from the cooling fluid conduit 20 a length of conduit that is substantially equal to the length of the valve containing body 23. This step forms a pair of spaced-apart fluid conduit ends which are spaced apart a distance substantially equal to the length of the valve containing body 23. The next step in this method of the invention comprises sealably interconnecting conduit end 20a with sleeve 22b of member 20 by any suitable means of a character well known to those skilled in the art. This done, conduit end 20b is sealably interconnected with sleeve 24b of member 24. When members 22 and 24 are threadably interconnected in the manner shown in FIGS. 7 and 8 and the assembly thus formed is repositioned within hollow body 16 in the manner shown in FIG. 3, a fluid flow path through the hollow body is formed to enable the flow of cooling fluid from the source of cooling fluid "S" through the adapter unit 70, through the valve means of the invention, and forwardly in the direction of the rotating tool 18. In the manner presently described, the unique construction of the valve means of the invention positively prevents back flow of the cooling fluid in a direction toward the source of cooling fluid "S".

Turning next to FIG. 10 through 14, an alternate embodiment of the dental-hand-piece assembly of the present invention is there illustrated. In this embodiment of the invention, the valve means is incorporated within the universal dental-hand-piece coupler assembly 17 rather than within the handle portion of the hand piece. Once again, the valve means of the invention is specially designed to be incorporated in the universal dental-hand-piece coupler as a part of a retrofit operation. As was the case with the earlier described form of the invention, the valve means can be incorporated into commercially available components with only minor modification thereto. In point of fact, the valve means can be sold separately as a part of a retrofit kit which can be used by owners of conventional dental hand pieces and universal dental-hand-piece couplings to retrofit the components to effectively prevent undesirable back flow of dental fluids toward the fluid supply lines.

Figure 12:
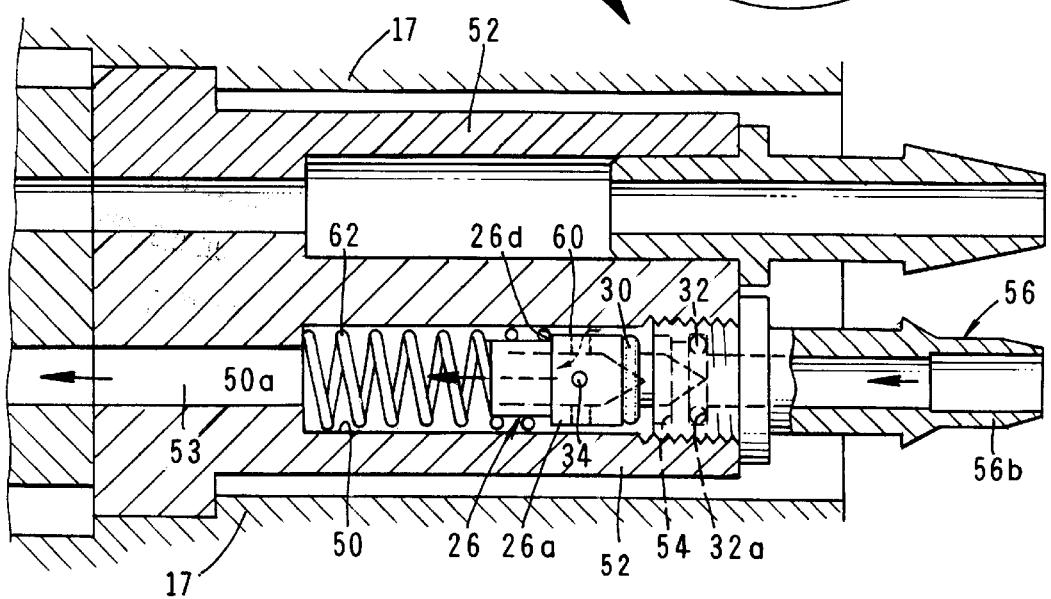
FIG. 12 is a cross-sectional view taken along lines 12—12 of FIG. 11 and is greatly enlarged to illustrate the details of construction of the one-way check valve assembly of this latest form of the invention.

As best seen in FIG. 13, the valve means of this latest form of the invention is similar to that shown in FIGS. 1 through 9, and like numerals are used to designate like components. However, in the instance where the adapter or coupler unit 17 is to be retrofitted, the valve assembly, which includes valve member 26, is disposed within a cavity 50 formed interiorly of the adapter body 52, rather than within a valve containing body such as body 23. Valve member 26 is reciprocally movable within cavity 50, which, in this case, is in the form of a counterbore made in adapter body 52, from a first valve-open position shown in FIG. 12, which permits fluid flow in a direction toward cutting tool 18, and a second valve-closed position shown in FIG. 13 wherein the valve member is in sealing engagement with a valve seat 54 provided on a threaded inlet fitting 56 which forms a part of the adapter assembly. Fitting 56 is threaded at its inboard end 56a and is adapted to be connected proximate its outboard end 56b within cooling fluid line (not shown) which is, in turn, connected to the source of cooling fluid "S". When valve member 26 is in the second position shown in FIG. 13, fluid flow in a direction toward the source of cooling fluid "S" is blocked. As best seen in FIGS. 12 and 13, valve member 26 includes an enlarged diameter portion 26a and a reduced diameter portion 26b, which portions join at a shoulder 26c. Circumscribing reduced diameter portion 26b is an elastomeric O-ring 30 which sealably engages seat 54 when the valve member is in the second valve closed position shown in FIG. 13. As illustrated in FIG. 13, when valve member 26 is in the second valve closed position, a second elastomeric O-ring 32 sealably engages the external, cylindrical surface 27 of reduced diameter portion 26b of the valve member. As before, when the valve is in the closed position, a double seal is provided to prevent leakage of fluid in a direction toward the source of cooling fluid "S".

Referring to FIGS. 13 and 14 it is to be noted that enlarged diameter portion 26a of valve member 26 is provided with a plurality of radially extending fluid passageways 34 which provide fluid flow passageways between the interior cavity 50 and the interior valve member 26. With this construction, when the valve means is in the open position shown in FIG. 12, fluid can flow through inlet component 56 into cavity 50, past elastomeric O-ring 30 and into a space 60 located between the interior wall of cavity 50 and valve member 26. From space 60, the cooling fluid can flow through radially extending flow passageways 34, into the interior of valve member 26, and then into flow channel 53 formed in body 52. However, when the valve means is closed, as shown in FIG. 9, flow in a direction toward cooling water source "S" is effectively blocked.

As before, biasing means, shown in the drawings as a coil spring 62, is disposed within cavity 50 and acts against shoulder 50a and 26d (FIG. 12) to continuously urge valve member 26 toward a valve-closed position. Spring 62 is constructed so that cooling water flowing through component 5 toward cutting tool 18 will overcome the urging of the spring and thereby maintain the valve in an open condition. However, any back flow of fluid in a direction toward the source "S" will cause the valve to automatically close.

In accordance with a second form of the method of the invention for retrofitting an autoclavable dental-hand-piece assembly, the valve means of the invention is once again interposed within the fluid flow path that extends through the dental-hand-piece assembly in the manner to prevent back flow of fluid in a direction toward the source "S" of the cooling fluid. However, in this second form of the method of the invention, the valve means is installed within the adapter unit 17. In accordance with this latter method of the invention, the first step in the accomplishment of this method involves cutting from body 52 of the adapter a cavity having a length substantially greater than the length of the valve member 26. In the present embodiment of the invention, this step is accomplished by forming a counterbore in body 54 which is coaxially aligned with fluid channel 53. As indicated in FIGS. 10 and 12, this counterbore is of a length such that the valve assembly, which comprises valve member 26, O-rings 30 and 32, and the biasing means or spring 62, can be operably disposed therewithin in the manner shown in the drawings. The inlet portion of the counterbore which defines cavity 50, is also threaded to enable the threaded interconnection of extremity threaded fitting 56 with body 52.

Once the cavity 50 is formed within body 52, in the manner described in the preceding paragraph, the valve assembly is operably positioned within the cavity. With valve body 26 and biasing spring 62 extending the length of the cavity in the manner shown in FIGS. 10, 12, and 13. With the valve assembly emplaced within cavity 50, fitting 56 is threadably interconnected with body 52 and the adapter or coupler 17 is interconnected with handle portion 16 of the dental hand piece.

The valve means of both forms of the invention as described in the preceding paragraphs is quite small. More specifically, the valve containing body 23 has a diameter on the order of 0.125 inches and a length of on the order of 0.50 inches or less. In the second embodiment of the invention, the valve member 26 has a length of on the order of only 0.16 inches or less and the biasing spring has a length of about 0.250 inches with the diameter of member 26 being about 0.078 inches.

Figure 15:
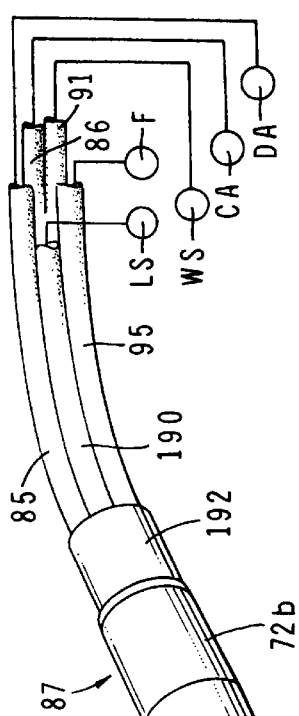
FIG. 15 is a generally perspective view of an alternate form of the dental-hand-piece assembly of the present invention.
Figure 16:
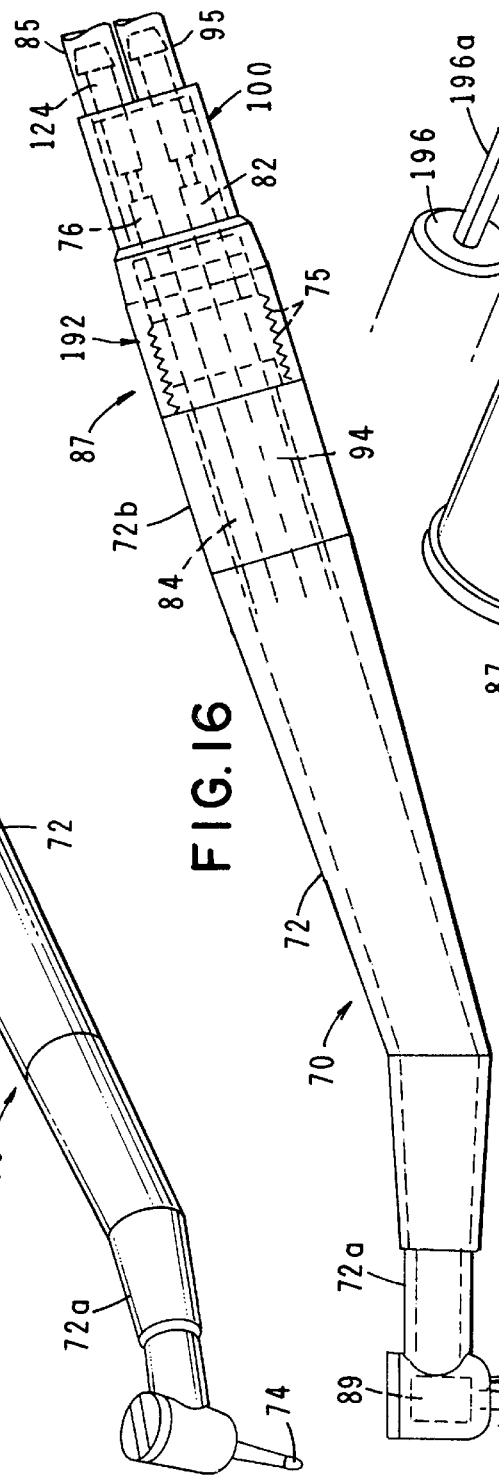
FIG. 16 is an enlarged, side-elevational view of the dental-hand-piece assembly illustrated in FIG. 15 with dotted lines showing internal construction and illustrating the manner of interconnection of the air and water supply lines with the basic dental hand piece.
Figure 17:
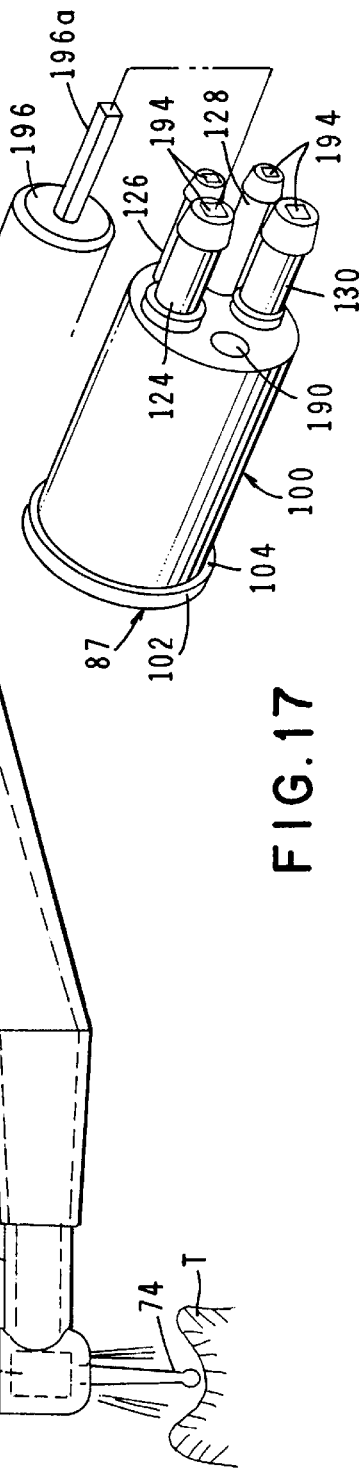
FIG. 17 is a greatly enlarged, generally perspective view of the novel, valve containing coupler assembly of the invention.
Figure 23:
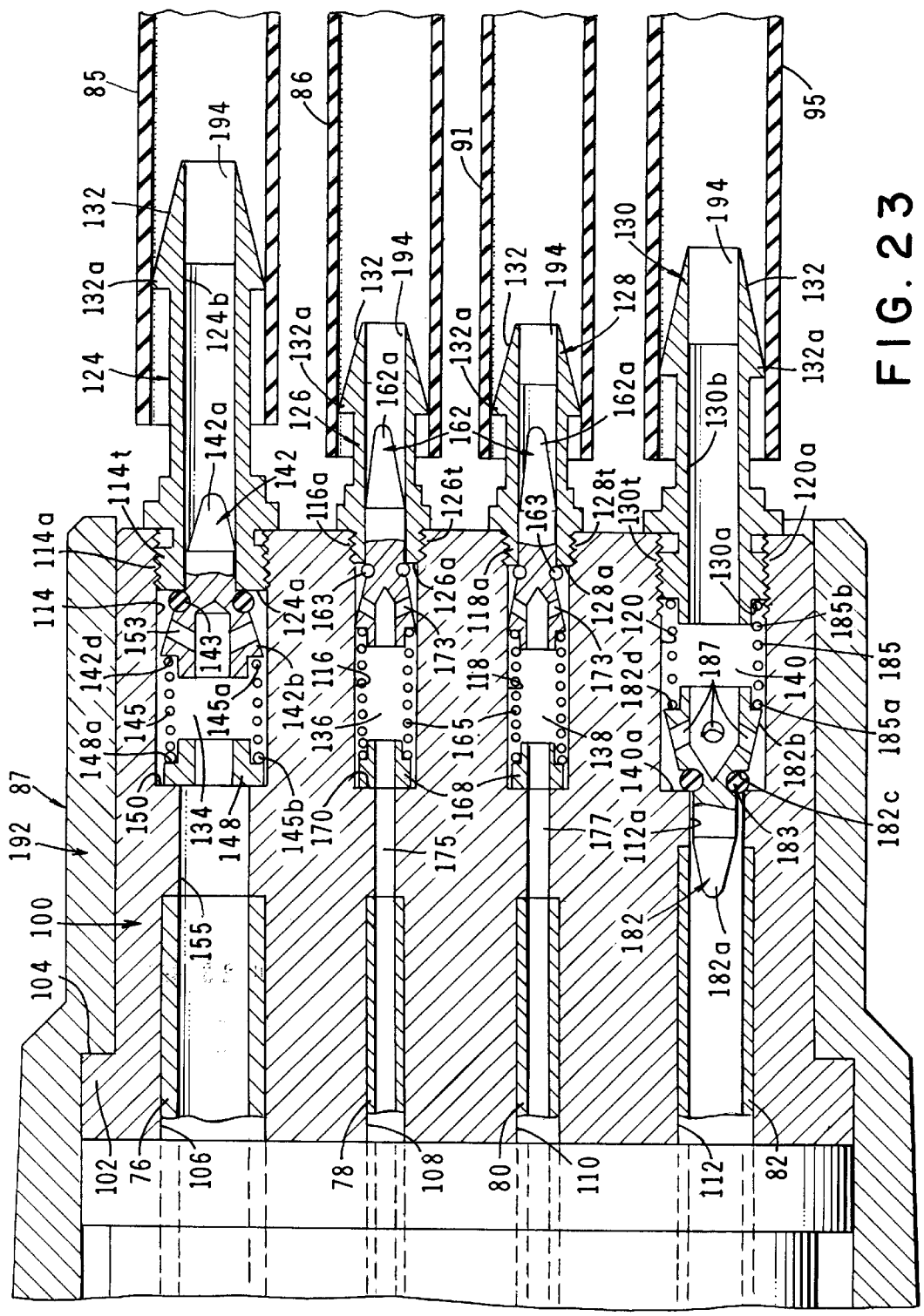
FIG. 23 is a greatly enlarged, cross-sectional view taken along lines 23—23 of FIG. 19 showing the details of construction of the various valve assemblies.

Turning next to FIGS. 15 through 30, an alternate form of the contamination-preventing apparatus of the invention is there illustrated. Once again, the hand piece, which is identified in FIG. 15 by the numeral 70, is of conventional construction and is capable of withstanding elevated temperatures sufficient to sterilize the entire assembly. As indicated in FIGS. 15 and 16, the hand piece comprises a hollow housing 72 having a first end 72a to which a rotatable cutting element 74 can be operably interconnected (FIG. 16). Cutting element 74 is rotated at very high speed by a conventional air turbine. Provided at the opposite, second end 72b of the hand piece are coupler connecting threads 75 and three outwardly extending hand-piece inlet connector tubes, namely a drive air inlet tube 76, a water inlet tube 78 and a chip air inlet tube 80 (FIG. 23). Also provided at second end 72b of the hand piece is an exhaust air outlet tube 82.

As best seen in FIG. 23, a conduit 84 is disposed internally of the hand piece assembly and extends from a location proximate first end 72a to a location proximate drive air inlet tube 76 so that it can communicate with a source of drive air "DA" via supply tube 85 and via the important coupler assembly 87 of the invention, the construction of which will presently be described. Drive air entering conduit 84 will flow along the length of the conduit and will be directed toward the air turbine 89 of the hand piece 70 (FIG. 16). A water conduit (not shown) is also disposed internally of the hand piece assembly and extends from the water inlet tube 78 to the forward end 72a of the hand piece. Water from the external water source "WS" can flow into water inlet tube 78 via supply tube 86 and via the coupler assembly. The water will then be carried by the water conduit to the forward end of the hand piece for use in cooling the rotating cutting element 74. A chip air conduit (not shown) is similarly disposed within the hand piece so that it can communicate with an external source of chip air "CA" via supply tube 91 and via coupler assembly 87.

To carry the exhaust air from turbine 89 to exhaust air outlet tube 82, a conduit 94 is provided within the hand piece assembly (FIG. 16). Conduit 94 communicates with an exhaust tube 95 via coupler assembly 87 in the manner best seen in FIG. 16.

Forming an extremely important aspect of the apparatus of the present invention is the universal, fully autoclavable coupler assembly of the invention which functions to interconnect the hand piece assembly 70 with the sources of drive air, water and chip air and with the exhaust tube 95. As best seen by referring to FIGS. 17, 18, 19, 23 and 24, the universal coupler assembly here comprises a generally cylindrical body 100 having an enlarged diameter and flange 102 which defines a shoulder 104. As shown in FIG. 23, body 100 is provided with first, second, third and fourth bores 106, 108, 110 and 112 respectively. With this construction, as the coupler assembly is connected to hand piece 70, bore 106 telescopically receives water inlet tube 76, bore 110 telescopically receives chip air tube 80 and bore 112 telescopically receives exhaust air tube 82.

Body 100 is also provided with first, second, third and fourth valve bores 114, 116, 118 and 120 respectively. For a purpose presently to be described, each of these valve bores is provided with internally threaded end portions, which end portions are designated in the drawings as 114a, 116a, 118a and 120a respectively. To interconnect drive air supply tube with coupler body 100, a first connector member 124 is provided. Similarly, a second connector member 126 is provided to connect water supply tube 86 with the coupler body and a third connector member 128 is provided to connect chip air supply tube 91 with the coupler body. To interconnect each of the connector members 124, 126 and 128 with body 100, each connector member is provided with a threaded extremity identified in the drawings as 124+, 126+ and 128+. Each of the connector member is also provided with a valve seat, which valve seats are designated in the drawings as 124a, 126a and 128a respectively.

To interconnect exhaust air tube 95 with coupler body 100, an outwardly extending fourth connector member 130 is provided. To enable interconnection with body 100, connector member 130 is also provided with a threaded end portion 130t. To ensure that a tight seal is formed between the various supply tubes and the connector members, each connector member is provided with a tapered end portion 132 which terminates in an enlarged diameter tube engaging edge 132a. With this construction, when the connector members are threadably interconnected with coupler body 100 in the manner shown in FIG. 23, four valve chambers 134, 136, 138, and 140 respectively are formed within body 100.

Disposed within valve bore 114 and chamber 134 is a drive air valve means which functions to permit turbine drive air to flow from the source of drive air "DA" toward bore 114, but positively prevents all air flow in the opposite direction, that is a direction toward supply tube 85. This important drive air valve means here comprises a valve member 142 which is reciprocally movable within bore 114 from the first valve-closed position shown in FIG. 23, to the second valve open position shown in FIG. 24. In this second valve open position, drive air can flow freely toward turbine 89. When valve member 142 is in the closed position, air flow in a direction toward supply tube 85 and toward the source of drive air is blocked.

Valve member 142 includes a first, bullet-like end portion 142a and a tapered portion 142b which joins portion 142a at an O-ring groove 142c (FIGS. 25 and 28). Disposed within and circumscribing ring portion 142c is sealing means here shown as an elastomeric O-ring 143 which sealably engages seat 124a when the valve member is in the valve closed position shown in FIG. 23. Biasing means, shown here as a coil spring 145 is disposed within valve chamber 134 and includes a first end 145a which acts against a shoulder 142d provided on valve member 142 in a manner to continuously urge valve member 142 toward the valve closed position shown in FIG. 23. The opposite end 145b of spring 145 acts against a shoulder 148a provided on a generally ring shaped valve member 148. Valve member 148, which also forms a part of the drive air valve means, is housed within chamber 134 and seats against an internal shoulder 150 formed proximate the inboard end of chamber 134.

Spring 145 is constructed so that the pressure exerted by drive air flowing through connector 124 toward air turbine 89 will overcome the urging of the spring and thereby maintain the valve in an open condition. However, any reverse pressure caused by the back flow of air in a direction toward the source "DA" will cause the valve to automatically close.

Referring to FIGS. 23, 25 and 28, it is to be noted that tapered portion 142b of valve member 142 is provided with a plurality of outwardly extending fluid passageways 153 which provide flow passageways between the interior of valve member 142 and valve chamber 134. With this construction, when the drive air valve means is in the open position shown in FIG. 24, turbine drive air can flow into passageway 124b of connector 124, past bullet-nose portion 142a of valve member 142 and into valve chamber 134. From chamber 134, the drive air can flow through flow passageways 153, into the interior of valve member 142, and then into a flow passageway 155 via ring-shaped valve member 148. From passageway 155, the drive air can flow into inlet tube 76 and then onwardly toward turbine 89. However, when the drive air valve means is closed, as shown in FIG. 23, flow in a direction toward drive air source "DA" is effectively blocked.

Disposed within valve bore 116 and chamber 136 is a cooling water valve means which functions to permit cooling water to flow from the source of cooling water "SW" toward bore 116, but positively prevents water flow in the opposite direction, that is a direction toward water supply tube 86. This important cooling water valve means is similar in construction to the previously described drive air valve means and here comprises a valve member 162 which is reciprocally movable within bore 116 from the first valve-closed position shown in FIG. 23, to the second valve open position shown in FIG. 24. In this second valve open position, cooling water can flow freely toward cutting tool 74. When valve member 162 is in the closed position, water flow in a direction toward supply tube 86 and toward the source of cooling water is blocked.

Valve member 162 includes a first, bullet-like end portion 162a and a tapered portion 162b (FIG. 26) which joins portion 162a at an O-ring groove 162c (FIGS. 25 and 28). Disposed within and circumscribing ring portion 162c is sealing means shown here as an elastomeric O-ring 163 which sealably engages seat 126a when the valve member is in the valve closed position shown in FIG. 23. Biasing means, shown here as a coil spring 165 is disposed within valve chamber 136 and includes a first end 165a which acts against a shoulder 142d provided on valve member 142 in a manner to continuously urge valve member 162 toward the valve closed position shown in FIG. 23. The opposite end 165b of spring 165 acts against a shoulder 168a provided on a generally ring shaped valve member 168. Valve member 168, which also forms a part of the cooling water valve means, is housed within chamber 136 and seats against an internal shoulder 170 formed proximate the inboard end of chamber 136.

Spring 165 is constructed so that the pressure exerted by cooling water flowing through connector 126 toward cutting tool 74 will overcome the urging of the spring and thereby maintain the valve in an open condition. However, any reverse pressure caused by the back flow of cooling water in a direction toward the source "WS" will cause the valve to automatically close.

As was the case with valve member 142, valve member 162 is provided with a plurality of outwardly extending fluid passageways 173 which provide flow passageways between the interior of valve member 162 and valve chamber 136. With this construction, when the cooling water valve means is in the open position shown in FIG. 24, cooling water can flow into passageway 126b of connector 126, past bullet-nose portion 162a of valve member 162 and into valve chamber 136. From chamber 136, the cooling water can flow through flow passageways 173 (FIG. 23), into the interior of valve member 162, and then into a flow passageway 175 via ring-shaped valve member 168. From passageway 175, the drive air can flow into inlet tube 78 and then onwardly toward cutting tool 74. However, when the cooling water valve means is closed, as shown in FIG. 23, flow in a direction toward cooling water source "WS" is effectively blocked.

Disposed within valve bore 118 and chamber 136 is a chip air valve means which functions to permit air to flow from the source of chip air "CA" toward bore 118, but positively prevents all air flow in the opposite direction, that is a direction toward supply tube 91. This chip air valve means is identical in construction to the cooling water valve means and identical numbers are used in the drawings to identify like components. More particularly, the chip air means comprises a valve member 162 which is reciprocally movable within bore 118 from the first valve-closed position shown in FIG. 23, to the second valve open position shown in FIG. 24. In this second valve open position, chip air can flow freely toward turbine 89. When valve member 162 is in the closed position, chip air flow in a direction toward supply tube 91 and toward the source of chip air is blocked.

Valve member 142 includes a first, bullet-like end portion 142a and a tapered portion 142b which joins portion 142a at an O-ring groove 142c (FIGS. 25 and 28). Disposed within and circumscribing ring portion 142c is sealing means here provided as an elastomeric O-ring 143 which sealably engages seat 124a when the valve member is in the valve closed position shown in FIG. 23. Biasing means, shown here as a coil spring 145 is disposed within valve chamber 134 and includes a first end 145a which acts against a shoulder 142d provided on valve member 142 in a manner to continuously urge valve member 142 toward the valve closed position shown in FIG. 23. The opposite end 145b of spring 145 acts against a shoulder 148a provided on a generally ring shaped valve member 148. Valve member 148, which also forms a part of the drive air valve means, is housed within chamber 134 and seats against an internal shoulder 150 formed proximate the inboard end of chamber 134.

Spring 165 of the chip air valve means is constructed so that the pressure exerted by chip air flowing through connector 128 toward cutting tool 74 will overcome the urging of the spring and thereby maintain the valve in an open condition. However, any reverse pressure caused by the back flow of chip air in a direction toward the source "CA" will cause the valve to automatically close.

Figure 24:
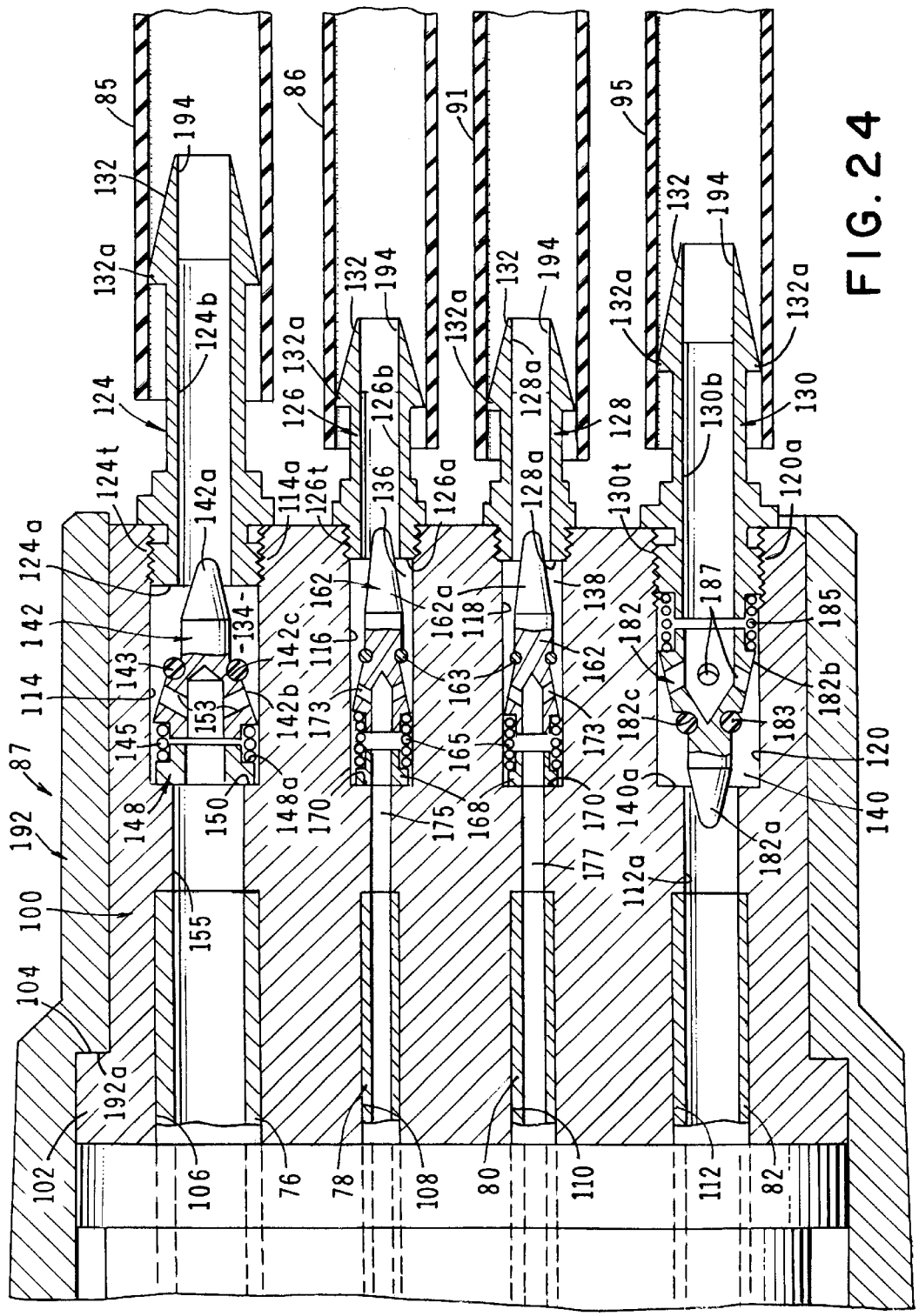
FIG. 24 is a cross-sectional view similar to FIG. 23, but showing the valve assemblies in an open position and showing the directions of fluid flow through the coupler assembly.
Figure 29:
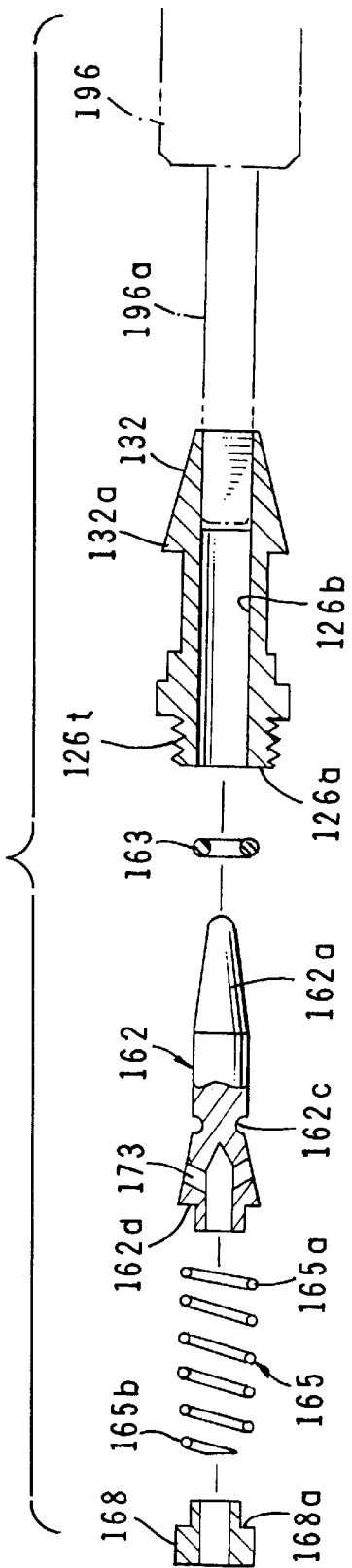
FIG. 29 is an enlarged, cross-sectional exploded view of the intermediate or second and third valves shown in FIG. 23.
Figure 30:
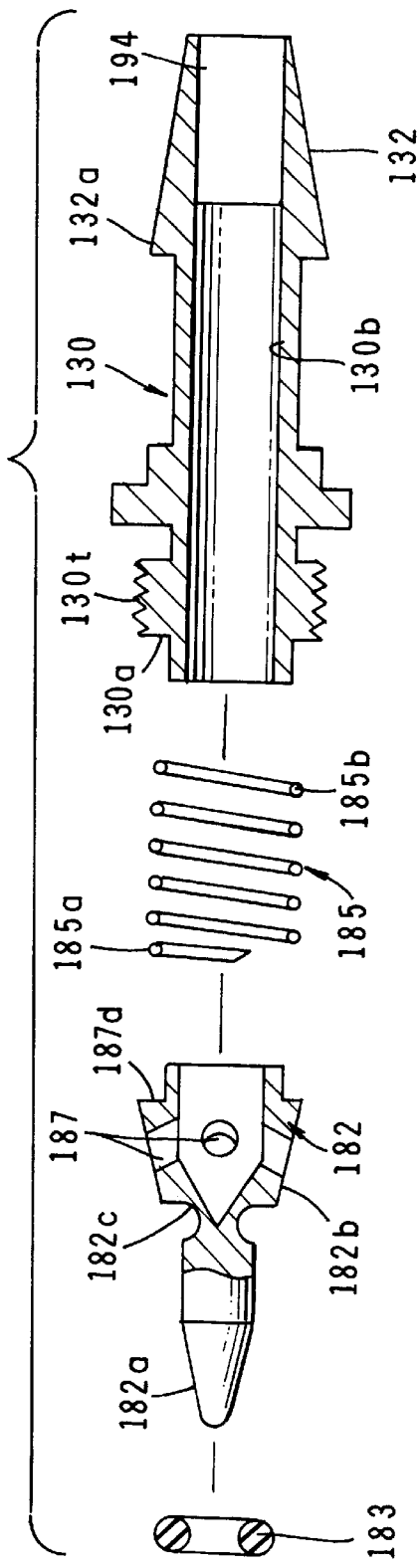
FIG. 30 is an enlarged, cross-sectional exploded view of the lower or fourth valve shown in FIG. 23.

Referring once again to FIGS. 23, 25 and 28, it is to be noted that, when the chip air valve means is in the open position shown in FIG. 24, chip air can flow into passageway 128b of connector 128, past bullet-nose portion 162a of valve member 162 and into valve chamber 138. From chamber 138, the chip air can flow through flow passageways 153, into the interior of chip air valve member 162, and then into a flow passageway 177 via ring-shaped valve member 168. From passageway 177, the chip air can flow into inlet tube 80 and then onwardly toward cutting tool. However, when the chip air valve means is closed, as shown in FIG. 23, flow in a direction toward drive air source "DA" is effectively blocked.

Disposed within valve bore 120 and chamber 140 is an exhaust air valve means which functions to permit exhaust air to flow from exhaust turbine 89 toward bore 120, but positively prevents all exhaust air flow in the opposite direction, that is a direction toward turbine 89. This important exhaust air valve means is of similar construction to the earlier described valve means and comprises a valve member 182 which is reciprocally movable within bore 120 from the first valve-closed position shown in FIG. 23, to the second valve open position shown in FIG. 24. In this second valve open position, turbine exhaust air can flow freely toward exhaust tube 95. However, when valve member 182 is in the closed position, exhaust air flow in a direction toward the hand piece 72 is blocked.

Valve member 182 includes a first, bullet-like end portion 182a and a tapered portion 182b which joins portion 182a at an O-ring groove 182c (FIGS. 25 and 28). Disposed within and circumscribing ring portion 182c is sealing means here shown as an elastomeric O-ring 183 which sealably engages a seat 140a when the valve member is in the valve closed position shown in FIG. 23. Seat 140 is formed proximate the inboard end of chamber 140 and is adjacent a reduced diameter flow passageway 112a (FIG. 23). Biasing means, shown here as a coil spring 185 is disposed within valve chamber 140 and includes a first end 185a which acts against a shoulder 182d provided on valve member 182 in a manner to continuously urge valve member 182 toward the valve closed position shown in FIG. 23. The opposite end 185b of spring 185 acts against a shoulder 130a provided on connector member 130.

Spring 185 is constructed so that the pressure exerted by the exhaust air flowing toward connector 130 from turbine 89 will overcome the urging of the spring and thereby maintain the valve in an open condition. However, any reverse pressure caused by the flow of exhaust air in a direction toward the hand piece 72 will cause the valve to automatically close.

Referring to FIGS. 23, 25 and 28, it is to be noted that, tapered portion 182b of valve member 182 is provided with a plurality of outwardly extending fluid passageways 187 which provide flow passageways between the interior of valve member 182 and valve chamber 140. With this construction, when the exhaust air valve means is in the open position shown in FIG. 24, turbine exhaust air can flow into exhaust tube 82, past bullet-nose portion 182a of valve member 182 and into valve chamber 140. From chamber 140, the exhaust air can flow through flow passageways 187, into the interior of valve member 182, and then into a flow passageway 130b of connector 13. From connector 130, the exhaust air can flow into tube 95 and to atmosphere via an appropriate filter (not shown). However, when the exhaust air valve means is closed, as shown in FIG. 23, flow in a direction toward an appropriately sterilized hand piece is effectively blocked.

As previously mentioned, the universal coupler of the invention, which is usable with all conventional commercially available hand pieces, is fully autoclavable. Accordingly, O-rings 143, 163, and 183 are constructed from viton which is a material that can withstand elevated temperatures. This viton material is available from various sources including Precision Associates, Inc. of Minneapolis, Minn.

In using the universal coupler assembly of the invention to interconnect a conventional hand piece such as the dental hand piece 72 with the various supply lines and with a fiber optic cable 190 (FIGS. 19 and 22) a simple connection means is provided. This connection means here comprises an internally threaded connector sleeve 192 which is slipped over body 100 in the manner shown in FIG. 18. This done, inlet connector tubes 76, 78, 80 and 82 are telescopically inserted into bores 106, 108, 110 and 112 respectively of body 100. Sleeve 192 is then threadably connected to external threads 75 of hand piece 72 and snugged down until an internal shoulder 192a formed on sleeve 92 engages shoulder 104 of coupler body 100. This tightening of sleeve 192 secures the coupler body to the hand piece in the manner shown in FIG. 23 with ends 190a and 190b of the fiber optic cable disposed in an abutting relationship (FIG. 22) so that light from an exterior light source "LS" be carried forwardly of the hand piece. With the hand piece and coupler body thus joined and with the various valve means in place as shown in FIG. 23, the supply tubes 85, 86, 91, and 95 can be sealably interconnected with connector members 124, 126, 128, and 130 respectively.

As previously mentioned, each of the connector members 124, 126, 128, and 130 is provided with a broached wrench receiving hole 194 which is configured to receive the stem 196a of a tightening wrench 196 (FIG. 20). Broached hole or opening 194 comprises a wrench receiving opening and forms a part of the means of the invention for imparting rotational movement to connector members 124, 126, 128, and 130. Wrench 196 can be used to conveniently remove any one of the connector members to gain access to chambers 134, 136, 138, and 140 so that the valve means housed therewithin can be quickly and conveniently removed for repair or replacement.

In the operation of the apparatus of this latest form of the invention, when coupler 87 is interconnected with supply tubes 85, 86, and 91 and with the dental hand piece by means of connection sleeve 192, a fluid flow path is formed through the dental hand piece assembly so that drive air will flow from the drive air source "DA" through tube 85, and into connector 124. The pressure of the drive air acting on the drive air valve means will open the valve allowing the drive air to flow freely to the air turbine. However, when the turbine is stopped, the flow of drive air will cease and the drive air valve means will automatically close thereby blocking reverse air flow toward tube 85.

Similarly, when the coupler is interconnected with the supply tubes and with the dental hand piece, a fluid flow path is formed through the dental hand piece assembly so that cooling water will flow from the water source "WS" through tube 86 and into connector 126. The pressure of the water acting on the cooling water valve means will open the valve allowing the water to flow freely toward the area of the cutting tool 74. However, when the water flow is stopped, the cooling water valve means will automatically close thereby blocking all reverse flow of water toward tube 86.

In like manner interconnection of the coupler with the hand piece will form a chip air flow path through the dental hand piece assembly so that chip air can flow from the chip air source "CA" through tube 91 and into connector 128. The pressure of the chip air acting on the chip air valve means will open the valve allowing the chip air to flow freely toward the area of the cutting tool. However, when flow of chip air is stopped, the chip air valve means will automatically close thereby blocking reverse flow toward tube 91.

When coupler 87 is interconnected with exhaust air tube 95 and with the dental hand piece by means of threaded sleeve 192, an exhaust air flow path is formed through the dental hand piece assembly so that exhaust air can flow from the air turbine toward the exhaust air valve means. The pressure of this exhaust air will cause the exhaust air valve means to open so as to allow the exhaust air to flow into exhaust tube 95 and then to atmosphere via filter "F". However, when the turbine is stopped, the flow of exhaust air will cease and the exhaust air valve means will automatically close thereby blocking flow of contaminants toward the hand piece at time of start-up.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A coupler assembly for use in interconnecting a dental hand piece with a source of air and with a source of water, the dental hand piece having an inlet end provided with connector threads and including an air inlet tube and a water inlet tube, said coupler assembly comprising:
   (a) a body having inlet bores for receiving the air inlet tube and water inlet tubes of the dental hand piece respectively and first and second valve bores, each said first and second valve bores having a valve receiving chamber and a threaded portion;
   (b) a first tube connector member threadably connected to said threaded portion of said first valve bore for interconnecting said body with the source of air, said first connector member having an internal bore and a valve seat and including means disposed within said internal bore for imparting rotational movement to said first connector member to gain access to said valve receiving chamber;
   (c) a second tube connector member threadably connected to said threaded portion of said second valve bore for interconnecting said body with the source of water, said second connector member having an internal bore and a valve seat and including means disposed within said internal bore for imparting rotational movement to said first connector member to gain access to said valve receiving chamber;
   (d) an air valve means disposed within said valve receiving chamber of said first valve bore for permitting air to flow from the source of air toward said air inlet tube of the dental hand piece, but preventing flow of air in an opposite direction, said air valve means comprising:
      (i) a valve member movable in a first direction from a valve open position to a valve closed position; and
      (ii) a spring in engagement with said valve member for urging said valve member toward said closed position;
   (e) a water valve means disposed within said valve receiving chamber of said second valve bore for permitting water to flow from the source of water toward the water inlet tube of the dental hand piece, but preventing flow of water in an opposite direction, said water valve means comprising:
      (i) a valve member movable in a first direction from a valve open position to a valve closed position; and
      (ii) a spring engagement with said valve member for urging said valve member toward said closed position;
   (f) connection means for connecting said body to said hand piece.

2. A coupler assembly as defined in claim 1 in which said connection means comprises a coupler sleeve slidably receivable over said body, said coupler sleeve having threads mateable with the connector threads of the hand piece to interconnect said body with the dental hand piece.

3. A dental hand piece assembly for interconnection with a source of air and with a source of water, said dental hand piece assembly comprising:
   (a) a housing having an inlet end proved with connector threads and including an air inlet tube and a water inlet tube;
   (b) a coupler assembly for interconnecting said housing with the source of air and with the source of water, said coupler assembly comprising:
      (i) a body having inlet bores for telescopically receiving said air inlet tube and said water inlet tube of said housing respectively and first and second valve bores, each said first and second valve bore having a threaded portion;
      (ii) a first tube connector member threadably connected to said threaded portion of said first valve bore for interconnecting said body with the source of air, said first connector member having a valve seat, a valve chamber and a tube connection extremity having an internal bore and means disposed within said internal bore for imparting rotation to said first connector member to gain access to said valve chamber;
      (iii) a second tube connector member threadably connected to said threaded portion of said second valve bore for interconnecting said body with the source of water, said second connector member having a valve seat;
      (iv) an air valve means disposed within said first valve bore for permitting air to flow from the source of air toward said air inlet tube, but preventing flow of air in an opposite direction;
      (v) a water valve means disposed within said second valve bore for permitting water to flow from the source of water toward said water inlet tube, but preventing flow of water in an opposite direction; and
      (vi) connection means for connecting said body with said housing.

4. A dental hand piece as defined in claim 3 in which said connection means comprises a coupler sleeve slidably receivable over said body, said coupler sleeve having threads mateable with said connector threads of said hand piece to interconnect said body with said housing.

5. A dental hand piece as defined in claim 3 in which each of said air valve means and said water valve means comprises:
   (a) a valve member movable in a first direction from a valve open position to a valve closed position; and
   (b) biasing means for continuously urging said valve member toward said valve closed position.

6. A dental hand piece as defined in claim 3 in which said housing further includes an exhaust air outlet tube and in which said body of said coupler assembly further comprises:
   (a) a body further including an exhaust air inlet bore for telescopically receiving the exhaust air outlet tube of the dental hand piece and an exhaust valve bore having a threaded portion and an exhaust valve seat;
   (b) a third connector member threadably connected to said threaded portion of said exhaust valve bore; and
   (c) an exhaust air valve means disposed within said exhaust valve bore for permitting exhaust air to flow from the exhaust air outlet of the dental hand piece toward said third connector member, but preventing flow in the opposite direction.

7. A dental hand piece as defined in claim 3 in which said housing of said dental hand piece further includes a fiber optic cable and in which said body of said coupler assembly further includes a fiber optic cable engageable with the fiber optic cable of said housing upon interconnection of said body with said housing.

8. A dental hand piece as defined in claim 3 in which each of said air valve means and said water valve means comprises a valve member having a bullet-like end portion and an integrally formed tapered portion, said tapered portion having a plurality of circumferentially spaced flow passageways.

9. A coupler assembly for use in interconnecting a dental hand piece with a source of air and with a source of water, the dental hand piece having an inlet end provided with connector threads and including an air inlet tube and a water inlet tube, said coupler assembly comprising:
   (a) a body having inlet bores for receiving the air inlet tube and water inlet tube of the dental hand piece respectively and first and second valve bores, each said first and second valve bore having an internal valve chamber and a threaded portion;
   (b) a first tube connector member threadably connected to said threaded portion of said first valve bore for interconnecting said body with the source of air, said first connector member having a valve seat and including a tube connection extremity having an internal bore and a broached hole formed in said internal bore for receiving a wrench adapted to impart rotational movement of said first tube connector member, whereby said first tube connector member can be disconnected from said body to gain access to said valve chamber;
   (c) a second tube connector member threadably connected to said threaded portion of said second valve bore for interconnecting said body with the source of water, said second connector member having a valve seat; and including a tube connection extremity having an internal bore and a broached hole formed in said internal bore for receiving a wrench adapted to impart rotational movement to said second tube connector member whereby said second tube connector member can be disconnected from said body to gain access to said valve chamber;
   (d) an air valve means disposed within said internal valve chamber of said first valve bore for permitting air to flow from the source of air toward said air inlet tube of the dental hand piece, but preventing flow of air in an opposite direction;
   (e) a water valve means disposed within said internal valve chamber of said second valve bore for permitting water to flow from the source of water toward the water inlet tube of the dental hand piece, but preventing flow of water in an opposite direction; and
   (f) connection means for connecting said body to said hand piece.

10. A coupler assembly for use in interconnecting a dental hand piece with a source of drive air, with a source of chip air, with a source of water and with an exhaust air tube, the dental hand piece having an inlet end provided with connector threads and including a drive air inlet tube, a chip air inlet tube, a water inlet tube and an exhaust air outlet tube, said coupler assembly comprising:
   (a) a body having a flange defining an external shoulder and first, second, third and fourth inlet bores for telescopically receiving the drive air inlet tube, the chip air inlet tube, the water inlet tube and the exhaust air outlet tube of the dental hand piece respectively and first, second, third and fourth valve bores, each said valve bore having a threaded end portion and said fourth valve bore having an exhaust valve seat;
   (b) first, second, third and fourth tube connector members threadably connected to said threaded portions of said first, second, third and fourth valve bores respectively for interconnecting said body with the source of drive air, the source of water, the source of chip air and with the exhaust air tube respectively, each of said first, second and third tube connector members having a valve seat and including a tube connection extremity having a broached hole for receiving a wrench adapted to impart rotational movement of said first tube connector member whereby said first tube connector member can be disconnected from said body;
   (c) a drive air valve means disposed within said first valve bore for permitting drive air to flow from the source of drive air toward said first inlet bore, but preventing flow of drive air in an opposite direction;
   (d) a water valve means disposed within said second valve bore for permitting water to flow from source of water toward said second inlet bore, but preventing flow of water in an opposite direction;
   (e) a chip air valve means disposed within said third valve bore for permitting chip air to flow from the source of chip air toward said third valve bore, but preventing flow of chip air in an opposite direction;
   (f) an exhaust air valve means disposed within said fourth valve bore for permitting exhaust air to flow from said fourth valve bore toward the exhaust air outlet tube, but preventing flow of exhaust air in an opposite direction; and
   (g) a coupler sleeve having a reduced diameter portion slidably receivable over said first portion of said body and an enlarged diameter portion having threads mateable with the connector threads of the hand piece for interconnection of said body with the dental hand piece.

11. A coupler assembly as defined in claim 10 in which each of said drive air valve means, said water valve means, and said chip air valve means comprises:
   (a) a valve member movable in a first direction from a valve open position to a valve closed position; and
   (b) biasing means for continuously urging said valve member toward said valve closed position.

12. A coupler assembly as defined in claim 11 in which each of said drive air valve means, said water valve means and said chip air valve means further includes sealing means carried by said valve member thereof for sealable engagement with said valve seats of said tube connector members.

13. A coupler assembly as defined in claim 12 in which said exhaust air valve means comprises:
   (a) an exhaust air valve member movable in a direction from a valve open position to a valve closed position; and
   (b) biasing means for continuously urging said exhaust air valve member toward said valve closed position.

14. A coupler assembly as defined in claim 13 in which said exhaust air valve means further includes sealing means carried by said exhaust air valve member for sealable engagement with said exhaust valve seat of said fourth valve bore.

15. A dental hand piece assembly for interconnection with a source of air and with a source of water, said dental hand piece assembly comprising:

(a) a housing having an inlet end provided with connector threads and including an air inlet tube and a water inlet tube;

(b) a coupler assembly for interconnecting said housing with the source of air and with the source of water, said coupler assembly comprising:

(i) a body having inlet bores for telescopically receiving said air inlet tube and said water inlet tube of said housing respectively and first and second valve bores, each said first and second valve bore having an internal chamber and a threaded portion;

(ii) a first tube connector member threadably connected to said threaded portion of said first valve bore for interconnecting said body with the source of air, said first connector member having a valve seat and extremity having a broached hole for receiving a wrench adapted to impart rotational movement to said first tube connector member, whereby said first tube connector member can be disconnected from said body to gain access to said internal chamber of said first valve bore;

(iii) a second tube connector member threadably connected to said threaded portion of said second valve bore for interconnecting said body with the source of water, said second connector member having a valve seat and including a tube connection extremity having a broached hole for receiving a wrench adapted to impart rotational movement to said first tube connector member, whereby said first tube connector member can be disconnected from said body to gain access to said second valve bore;

(iv) an air valve means disposed within said first valve bore for permitting air to flow from the source of air toward said air inlet tube, but preventing flow of air in an opposite direction said air valve means comprising a valve body and biasing means for urging said valve body toward said valve seat of said first connector member;

(v) a water valve means disposed within said internal chamber of said second valve bore for permitting water to flow from the source of water toward said water inlet tube, but preventing flow of water in an opposite direction, said water valve means comprising a valve body and biasing means for urging said valve body toward said valve seat of said second connector member; and (vi) connection means for connecting said body with said housing.

16. A coupler assembly for use in interconnecting a dental hand piece with a source of fluid, the dental hand piece having an inlet end provided with connector threads and including a fluid inlet tube, said coupler assembly comprising:

(a) a body having an inlet bore for receiving the fluid inlet tube and a first valve bore, having a valve chamber and a threaded portion;

(b) a first tube connector member threadably connected to said threaded portion of said first valve bore for interconnecting said body with the source of fluid, said first connector member having a valve seat and including a tube connection extremity having an elongated bore and means within said elongated bore for imparting rotational movement to said first tube connector member, whereby said first tube connector member can be threadably disconnected from said body to gain access to said valve chamber;

(c) valve means disposed within said valve chamber of said first valve bore for permitting fluid to flow from the source of fluid toward said fluid inlet tube of the dental hand piece, but preventing flow of air in an opposite direction; and (d) connection means for connecting said body to said hand piece.

17. A coupler assembly as defined in claim 16 in which said means for imparting rotational movement to said first tube connector comprises a wrench receiving opening formed internally of said tube connection extremity of said first connector member.

18. A coupler assembly as defined in claim 16 in which said means for imparting rotational movement to said first tube connector comprises a wrench receiving broached hole.

19. A coupler assembly for use in interconnecting a dental hand piece with a source of air and with a source of water, the dental hand piece having an inlet end provided with connector threads and including an air inlet tube and a water inlet tube, said coupler assembly comprising:

(a) a body having inlet bores for receiving the air inlet tube and water inlet tube of the dental hand piece respectively and first and second valve bores, each said first and second valve bore having a valve chamber and a threaded portion;

(b) a first tube connector member threadably connected to said threaded portion of said first valve bore for interconnecting said body with the source of air, said first connector member having an internal bore and a valve seat and including a tube connection extremity having means disposed within said internal bore of said first tube connector for imparting rotational movement to said first tube connector member, whereby said first tube connector member can be disconnected from said body to gain access to said valve chamber;

(c) a second tube connector member threadably connected to said threaded portion of said second valve bore for interconnecting said body with the source of water, said second connector member having an internal bore and a valve seat; and including a tube connection extremity having means disposed within said internal bore of said second tube connector for imparting rotational movement to said second tube connector member whereby said second tube connector member can be disconnected from said body to gain access to said valve chamber;

(d) an air valve means disposed within said first valve bore for permitting air to flow from the source of air toward said air inlet tube of the dental hand piece, but preventing flow of air in an opposite direction said air valve means comprising a body portion and a coiled spring in engagement with said body portion;

(e) a water valve means disposed within said second valve bore for permitting water to flow from the source of water toward the water inlet tube of the dental hand piece, but preventing flow of water in an opposite direction said water valve means comprising a valve body and a coiled spring in engagement with said body portion; and (f) connection means for connection said body to said hand piece.

20. A coupler assembly as defined in claim 19 in which said means for imparting rotational movement to said first tube connector comprises a broached wrench receiving opening formed interiorly of said tube connection extremity of said first connector member and in which said means for imparting rotational movement of said second tube connector comprises a broached wrench receiving opening formed in said tube connection extremity of said second connector member.

* * * * *